US009138184B2

(12) United States Patent
Lum

(10) Patent No.: US 9,138,184 B2
(45) Date of Patent: Sep. 22, 2015

(54) CONTACT ACTIVATED INCISION DEVICE

(76) Inventor: Wah Leong Lum, Singapore (SG)

( * ) Notice: Subject to any disclaimer, the term of this patent is extended or adjusted under 35 U.S.C. 154(b) by 0 days.

(21) Appl. No.: 13/045,645

(22) Filed: Mar. 11, 2011

(65) Prior Publication Data

US 2012/0179185 A1 Jul. 12, 2012

(30) Foreign Application Priority Data

Jan. 7, 2011 (SG) ................................. 201100089

(51) Int. Cl.
*A61B 17/14* (2006.01)
*A61B 17/32* (2006.01)
*A61B 5/15* (2006.01)
*A61B 5/151* (2006.01)

(52) U.S. Cl.
CPC ......... *A61B 5/150022* (2013.01); *A61B 5/1411* (2013.01); *A61B 5/1433* (2013.01); *A61B 5/15109* (2013.01); *A61B 5/15117* (2013.01); *A61B 5/15128* (2013.01); *A61B 5/15144* (2013.01); *A61B 5/150442* (2013.01); *A61B 5/150587* (2013.01); *A61B 5/150717* (2013.01); *A61B 5/150893* (2013.01); *A61B 5/150916* (2013.01)

(58) Field of Classification Search
CPC ........... A61B 17/32093; A61B 5/1411; A61B 5/15142; A61B 5/15186; A61B 5/15188; A61B 5/14532; A61B 5/151; A61B 5/15101; A61B 5/15103; A61B 5/15105; A61B 5/15107; A61B 5/15109; A61B 5/15111; A61B 5/15113; A61B 5/15115; A61B 5/15117; A61B 5/15128; A61B 5/15132; A61B 5/15194; A61B 5/150442; A61B 5/15144; A61B 5/150916; A61B 5/150893; A61B 5/150717; A61B 5/150587
USPC .......... 606/167, 181–185; 600/562, 564, 583, 600/573, 576, 563, 566–568; 30/426, 427, 30/418, 420; 604/71, 73
See application file for complete search history.

(56) References Cited

U.S. PATENT DOCUMENTS

| | | | | |
|---|---|---|---|---|
| 5,314,441 | A | * | 5/1994 | Cusack et al. ................. 606/182 |
| 5,571,132 | A | | 11/1996 | Mawhirt |
| 5,643,306 | A | * | 7/1997 | Schraga ......................... 606/182 |
| 5,951,582 | A | * | 9/1999 | Thorne et al. ................. 606/182 |
| 7,452,365 | B2 | * | 11/2008 | Galloway et al. ............. 606/167 |
| 2007/0095178 | A1 | * | 5/2007 | Schraga ............................ 83/13 |

FOREIGN PATENT DOCUMENTS

WO    WO 2010/014044 A1    2/2010

* cited by examiner

*Primary Examiner* — Jocelin Tanner
(74) *Attorney, Agent, or Firm* — Porter, Wright, Morris & Arthur, LLP

(57) ABSTRACT

A contact activated incision device, comprises a housing defining a cavity, and a longitudinal axis extends between a proximal end and a distal end of the housing. A slider is slidable with respect to the housing along the longitudinal axis and at least partially positioned outside of the housing. A roller is mounted on the housing and rotatable about an axis perpendicular to the longitudinal axis. A blade assembly is mounted on the roller and has a blade, wherein the blade is movable from a retracted position to an extended position and to a final position, at the retracted position the blade is positioned in the cavity, at the extended position the blade extends at least partially beyond the proximal end of the housing, and at the final position the blade is positioned in the cavity.

19 Claims, 8 Drawing Sheets

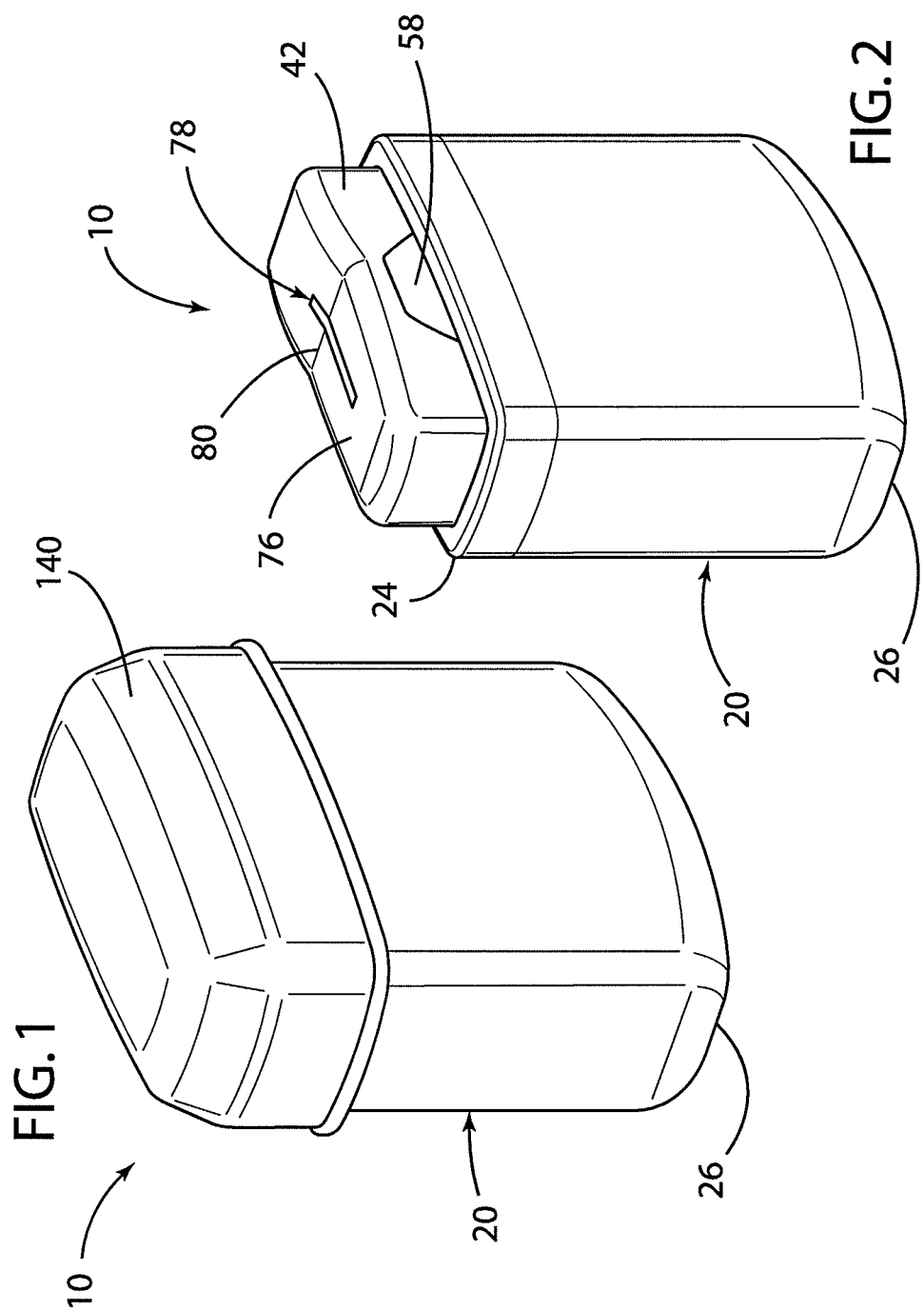

US 9,138,184 B2

CONTACT ACTIVATED INCISION DEVICE

FIELD OF THE INVENTION

The present invention relates to the field of incision devices for drawing blood samples. More particularly, it relates to a contact activated incision device for drawing blood samples from patients.

BACKGROUND OF THE INVENTION

Blood samples are drawn from patients for various diagnostic tests. The blood samples are usually drawn by incision procedures on the patient's skin. Known devices for drawing blood include, for example, United States Patent Application Publication 2010/0076472 A1 to Sun which discloses a device for performing an incision on a patient's skin. In use, the device is activated by a hand or finger of a user operating a trigger on one side of the device. When the trigger is operated, a blade extends from an opposite side so as to cut the patient's skin.

U.S. Pat. No. 5,951,582 to Thorne et al discloses a push activated lancet apparatus. In use, the device is activated by pushing a button at the top of device by a user and a blade extends from a front side of the device to cut the patient's skin.

U.S. Pat. No. 6,221,089 to Mawhirt discloses another device for making an incision in the skin. The device has a finger engageable trigger located external to the housing for actuating the triggering mechanism. A finger of the user pushes the trigger in one direction on one side of the device and a blade extends from a side parallel to the direction of push of the trigger.

U.S. Pat. No. 5,314,441 to Cusack discloses a slicing lancet assembly which has a similar triggering mechanism as in Mawhirt. A finger of the user pushes the trigger in one direction on one side of the device and a blade extends from a side parallel to the direction of push of the trigger.

Singapore Patent Publication 152088 to Lum discloses a contact activated lancet device. In use, a user places the device against a patient's skin and pushes a lancet holder into the device, causing the lancet holder to rotate about a longitudinal axis until it clears a driver and extends out of a housing, where a lance or needle punctures the patient's skin.

As mentioned above, known contact activated incision devices generally use puncturing action to provide an incision on the patient's skin. The force applied to the patient's skin may not be uniform on the area of the applied surface. Some training may also be required on the part of a medical worker who applies the device to the patient. As such, it would be desirable to provide a contact activated incision device which is easy to use, is designed for consistent application, requires little training, resists accidental firing and has wide operating tolerances.

SUMMARY OF THE INVENTION

In accordance with a first aspect, a contact activated incision device, comprises a housing, slider, roller and blade assembly. The housing defines a cavity, and a longitudinal axis extends between a proximal end and a distal end of the housing. A slider is slidable with respect to the housing along the longitudinal axis and at least partially positioned outside of the housing. A roller is mounted on the housing and rotatable about an axis perpendicular to the longitudinal axis. A blade assembly is mounted on the roller and has a blade, wherein the blade is movable from a retracted position to an extended position and to a rest position, at the retracted position the blade is positioned in the cavity, at the extended position the blade extends at least partially beyond the proximal end of the housing, and at the rest position the blade is positioned in the cavity.

In accordance with another aspect, the contact activated incision device has a housing defining a cavity and a longitudinal axis. The longitudinal axis extends between a proximal end and a distal end. A slider is slidable with respect to the housing along the longitudinal axis. The slider is at least partially positioned outside of the housing. A first biasing means is positioned between the housing and the slider. The first biasing means abuts the slider and biases the slider towards the proximal end. A roller is mounted on the housing and is rotatable with respect to the housing. A blade assembly is mounted on the roller. The blade assembly has a blade and the blade is movable from a retracted position to an extended position and to a rest position. At the retracted position the blade is positioned in the cavity, at the extended position the blade extends at least partially beyond the proximal end of the housing, and at the rest position the blade is positioned in the cavity.

From the foregoing disclosure and the following more detailed description of various embodiments it will be apparent to those skilled in the art that the present invention provides a significant advance in the technology of contact activated incision devices. Particularly significant in this regard is the potential the invention affords for providing a contact activated incision device operable with wide part tolerances. Additional features and advantages of various embodiments will be better understood in view of the detailed description provided below.

BRIEF DESCRIPTION OF THE DRAWINGS

FIG. 1 is an isometric view of one embodiment of the contact activated incision device with a cap attached.

FIG. 2 shows the device of FIG. 1 with the cap removed and ready to be used.

Figure 3:
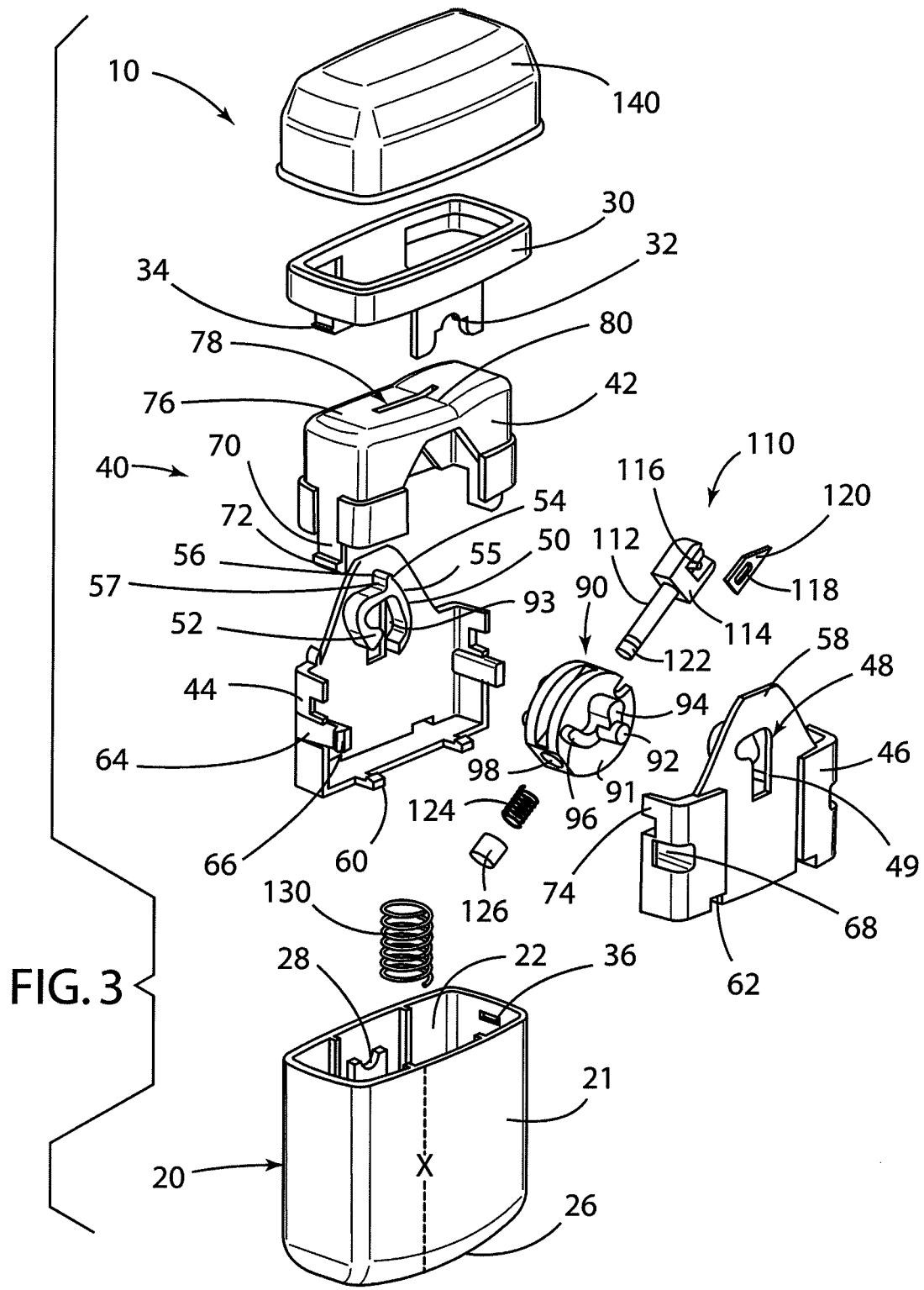
FIG. 3 is an exploded isometric view of the device of FIG. 1.

It should be understood that the appended drawings are not necessarily to scale, presenting a somewhat simplified representation of various features illustrative of the basic principles of the invention. The specific design features of the contact activated incision device as disclosed here, including, for example, the specific dimensions of the cam ledge and cam surface, will be determined in part by the particular intended application and use environment. Certain features of the illustrated embodiments have been enlarged or distorted relative to others to help provide clear understanding. In particular, thin features may be thickened, for example, for clarity of illustration. All references to direction and position, unless otherwise indicated, refer to the orientation illustrated in the drawings.

DETAILED DESCRIPTION OF PREFERRED EMBODIMENT(S)

It will be apparent to those skilled in the art, that is, to those who have knowledge or experience in this area of technology, that many uses and design variations are possible for the contact activated incision device disclosed here. The following detailed discussion of various alternate features and embodiments will illustrate the general principles of the invention with reference to a contact activated incision device suitable for use as a heelstick. Other embodiments suitable for other applications will be apparent to those skilled in the art given the benefit of this disclosure.

Turning now to Figs., FIG. 1 shows a contact activated incision device 10. The device 10 has a cap 140, and a housing 20. The cap 140 is releasably secured to a proximal end 24 of the housing. In FIG. 2 the cap is removed, revealing a slider top 42 and an opening 78 sitting in a depression 80 which is located at a top 76 of the slider top 42. The slider top 42 has a lip 58 which is visible to a user before the device is used. The housing 20 extends from the proximal end 24 to a distal end 26.

FIG. 3 is an exploded isometric view of the contact activated incision device 10. The device comprises a housing 20 optionally formed from top housing 30 and bottom housing 21, a slider 40 optionally formed from a slider top 42, a first slider body 44 and a second slider body 46, a roller 90 and a blade assembly 110. The housing 20 and slider 40 may be formed from multiple components fastened together or each as a single component. Top housing 30 and bottom housing 21 may be connected by snap fit, for example by flexible arm 34 resiliently engaging groove 36. Also, the first slider body 44 and second slider body 46 may be connected by snap fit, for example by arm 64 engaging groove 68 at finger 66. Alternatively the slider bodies may be formed of a one piece or unitary construction and connected by a living hinge, for example. Further, slider top 42 may also be connected by snap fit to the other parts of the slider, for example by arm 70 with finger 72 engaging groove partially defined by surface 74.

The housing defines a cavity 22 and top housing 30 has a restriction portion and bottom housing 21 has a rest portion which cooperates with the restriction portion when assembled together to receive shafts 92 of the roller. Thus, the roller is rotatably mounted on the housing. The slider 40 is received in the cavity 22 and is slidable with respect to the housing. A first biasing means such as spring 130 is positioned between the slider and the housing.

Each of the first and second slider bodies 44, 46 has a cam ledge 50. The cam ledge 50 has a first wall 55, a protrusion 54, a second wall 57, and a flange 52. The protrusion 54 has a tip 56. The slider has a slot 48 having perimeter 49. The cam ledge is partially coterminal with the perimeter 49, but is separate by a gap 93 on each slider body. The gap allows for relative movement of the roller with respect to the slider during operation.

The roller 90 is positioned within the slider between the cam ledges 50 of slider bodies 44 and 46. The roller 90 has a cam surface 96, a pair of shafts 92 and 94 on each side of the roller body 91. Shaft 92 is longer than shaft 94. Roller 90 has a channel 98 for holding blade assembly 110. The channel 98 allows the blade assembly 110 to be mounted partially within the roller 90. Blade assembly 110 has head portion 114, an intermediate portion 112 and a tail portion 122. The roller has a main body 91 with a channel 98. The intermediate portion 112 of the blade assembly is mounted within the channel 98. Blade 120 is mounted to the head portion 114 and slidable with respect to the roller. Projections 116 extend from the head portion 114. A second biasing means such as spring 124 is positioned between the roller and a stopper 126 at the tail portion 122. The stopper has a width larger than the channel and thereby resists separation of the blade assembly from the roller, in one direction. In the other direction the projections 116 resist separation of the blade assembly from the roller.

Figure 4:
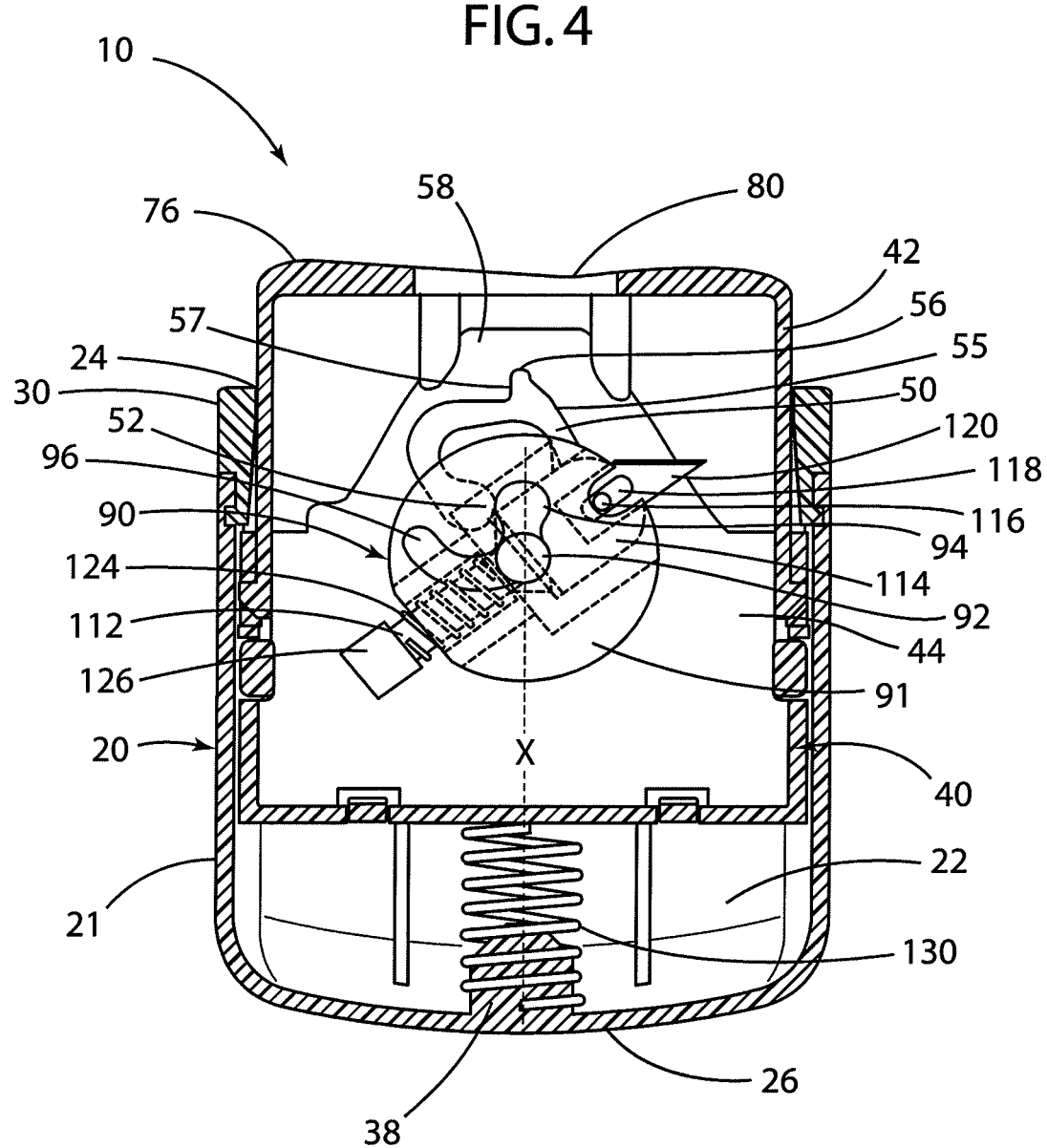
FIG. 4 a cross section view of the device of FIG. 1 when a roller is at a start position.

FIG. 4 shows the device after the cap has been removed but prior to activation. A longitudinal axis X extends between the proximal end 24 and the distal end 26 of the housing 20. The slider is slidable along the longitudinal axis X from a first position to a second position and to a third position. As shown in the Figs., the slider is at least partially positioned outside of the housing. FIG. 4 shows the device 10 before it is activated with the slider at the first position. The first biasing means 130 biases the slider 40 towards the first position. The first biasing means abuts the slider and biases the slider towards the proximal end 24. The lip 58 is positioned above the housing 20 (with respect to the plane of the paper of FIG. 4) and is visible to a user when the slider is in the first position. When the slider is in the third position, the lip is positioned within the cavity and not visible from outside the housing. Optionally the lip may be formed of a material having a colour contrasting with the housing so that the lip acts as an indicator of whether the device has been used.

The blade 120 is biased away from an extended position and towards a retracted position by the second biasing means 124. Projections 116 abut against first walls 55 of cam ledges 50 of slider 40, resisting further retraction of the blade. The roller can rotate from a start position to an apex position and to a post-apex segment about an axis perpendicular to the longitudinal axis X. When the slider is in the first position as shown in FIG. 4, the roller 90 is in the start position and is at an acute angle with respect to the X axis. First biasing means 130 sits on mount 38 and is shown to be largely uncompressed.

Figure 5:
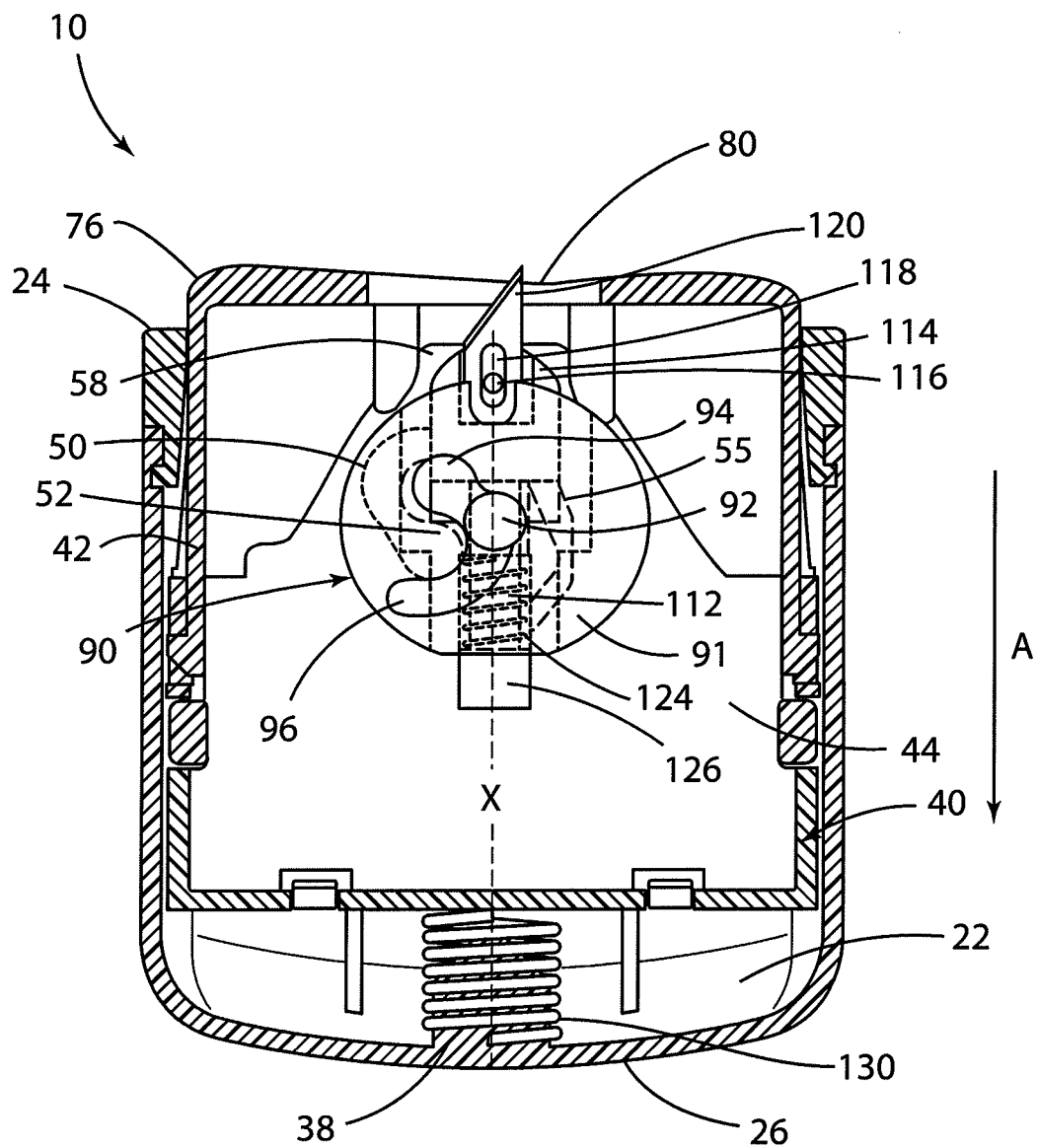
FIG. 5 a cross section view of the device of FIG. 1 when a roller is at an apex position.

FIG. 5 shows the blade 120 deployed in the extended position, the roller is in the apex position, and the slider is in the second position. Movement to these positions is achieved by contact activation. That is, the slider 20 is positioned against a patient's skin at the proximal end 24 of the housing 20. Pushing the housing 20 towards the patient's skin compresses the first biasing means 130, and urges the slider 40 into the housing 20 and towards the second position in the direction marked as A in FIG. 5. The slider eventually engages the roller (flange 52 of cam ledge 50 engages cam surface 96) urging the roller to rotate. As the roller rotates the projections 116 travel along the first walls 55 of the cam ledges 50 of the slider 40 until they reach the tip 56 of protrusion 54. As first wall 55 is non-circular at protrusion 54, the blade both rotates with the roller and translates away from the axis of rotation of the roller. Advantageously, this urges the blade to extend out of the opening in the slider as shown in FIG. 5.

Figure 6:
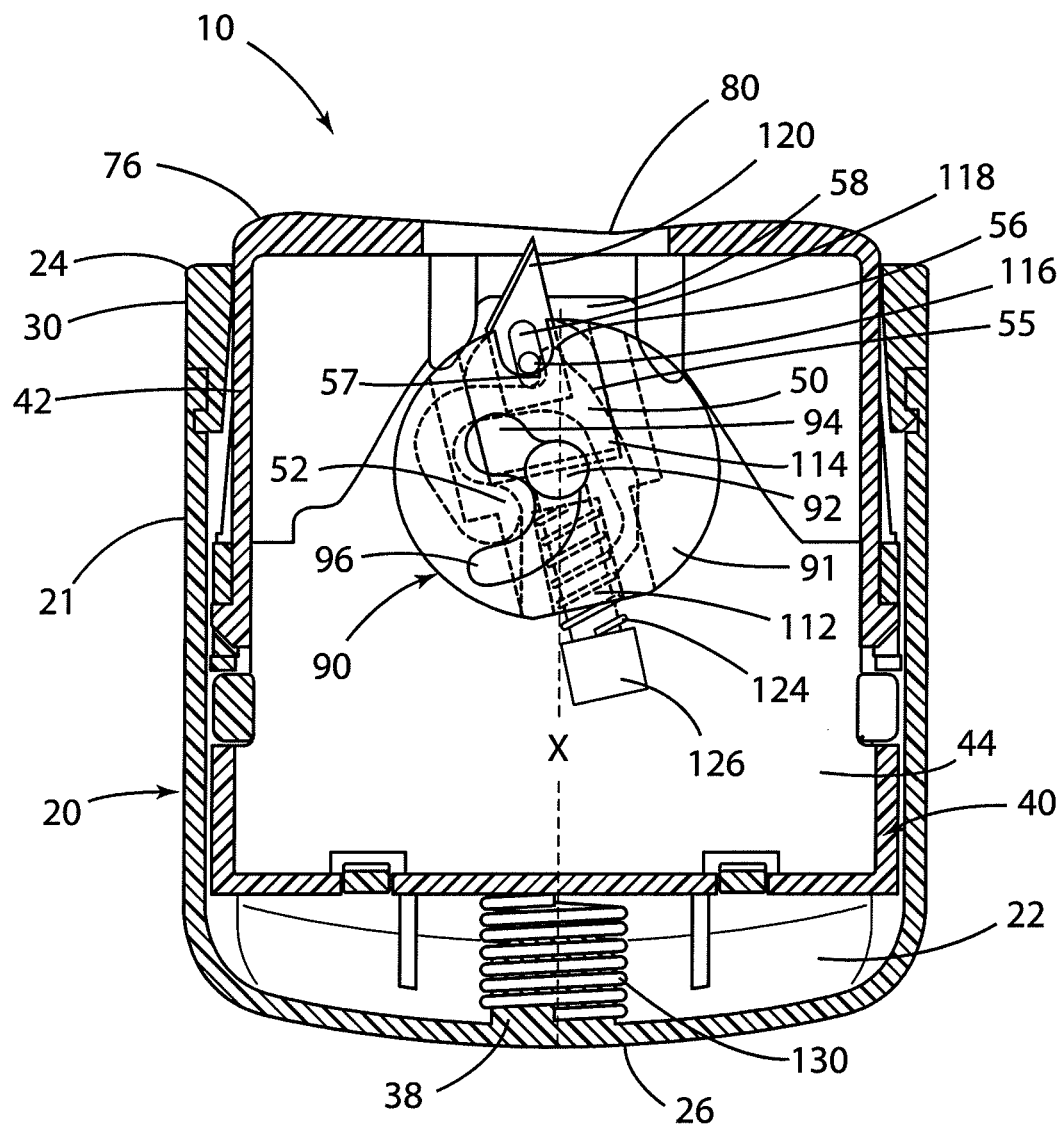
FIG. 6 a cross section view of the device of FIG. 1 when a roller is at a post-apex segment.

FIG. 6 shows continued anticlockwise rotation of the roller 90 to the post-apex segment in response to movement of the slider to the third position. The slider is in the third position and the blade is shown retracted back within the slider 40. In the third position the slider further compresses first biasing member 130. In accordance with an advantageous feature, at the retracted position the blade is positioned in the cavity, at the extended position the blade extends at least partially beyond the proximal end of the housing, and at the final position the blade is positioned in the cavity. The cam ledge 50 is positioned between the roller 90 and the projections 116 such that as the slider 40 slides from the first position to the second position, the roller rotates, and the blade translates away from the roller. Rotation of the roller 90 past the apex position to a post-apex segment causes the projection 116 to move past the tip 56 and past the second wall 57. This allows the second biasing means 124 to pull the blade 120 back towards the axis of rotation to the final position. Movement of the roller back from the post-apex segment to the apex position is thwarted by projections abutting second wall 57.

Figure 7:
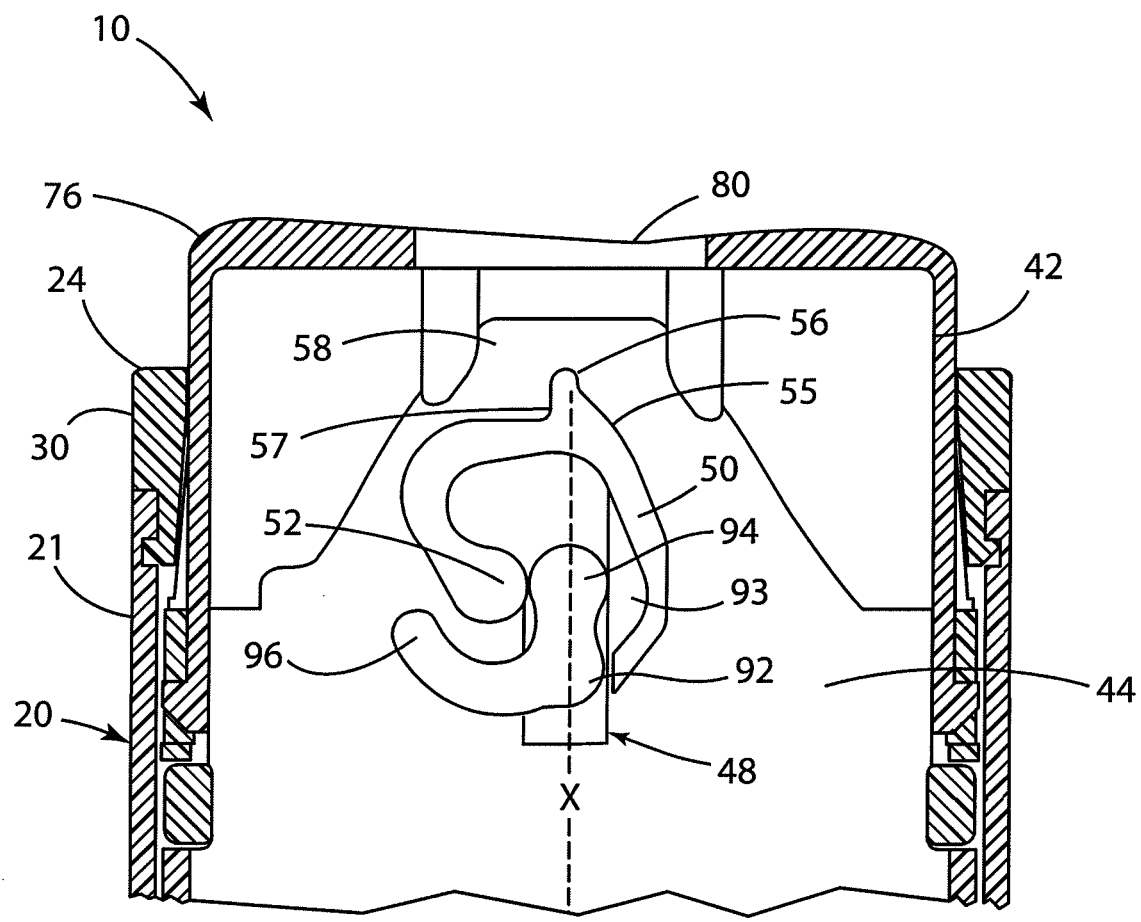
FIG. 7 is simplified schematic view showing the relative position of a cam surface of the roller and a cam ledge of a slider when the roller is at the start position.

FIG. 7 is a simplified schematic which shows the interrelationship of the cam ledge 50, cam surface 96, slot 48 and shafts 92 and 94. FIG. 7 is like FIG. 4 where the slider is in the first position, the roller is in the start position and the blade is in the retracted position. Shafts 92 are captivated by rest portion 28 and restriction portion 32 of the housing, thus, the roller can only rotate with respect to the housing. Shafts 92 and 94 are positioned in slot 48. As shown in FIG. 7, the shafts 92, 94 engage the perimeter of the slot 48 to resist rotation of the roller in a clockwise direction. Note also that there is a space between flange 52 and cam surface 96. Thus, the slider does not engage the roller until flange 52 moves into contact with cam surface 96, and the roller cannot rotate from the start position until the slider has moved from the first position. Once flange 52 has engaged cam surface 96, the slider has engaged the roller, and continued sliding of the slider toward the second position urges the roller to rotate from the start position toward the apex position.

Figure 8:
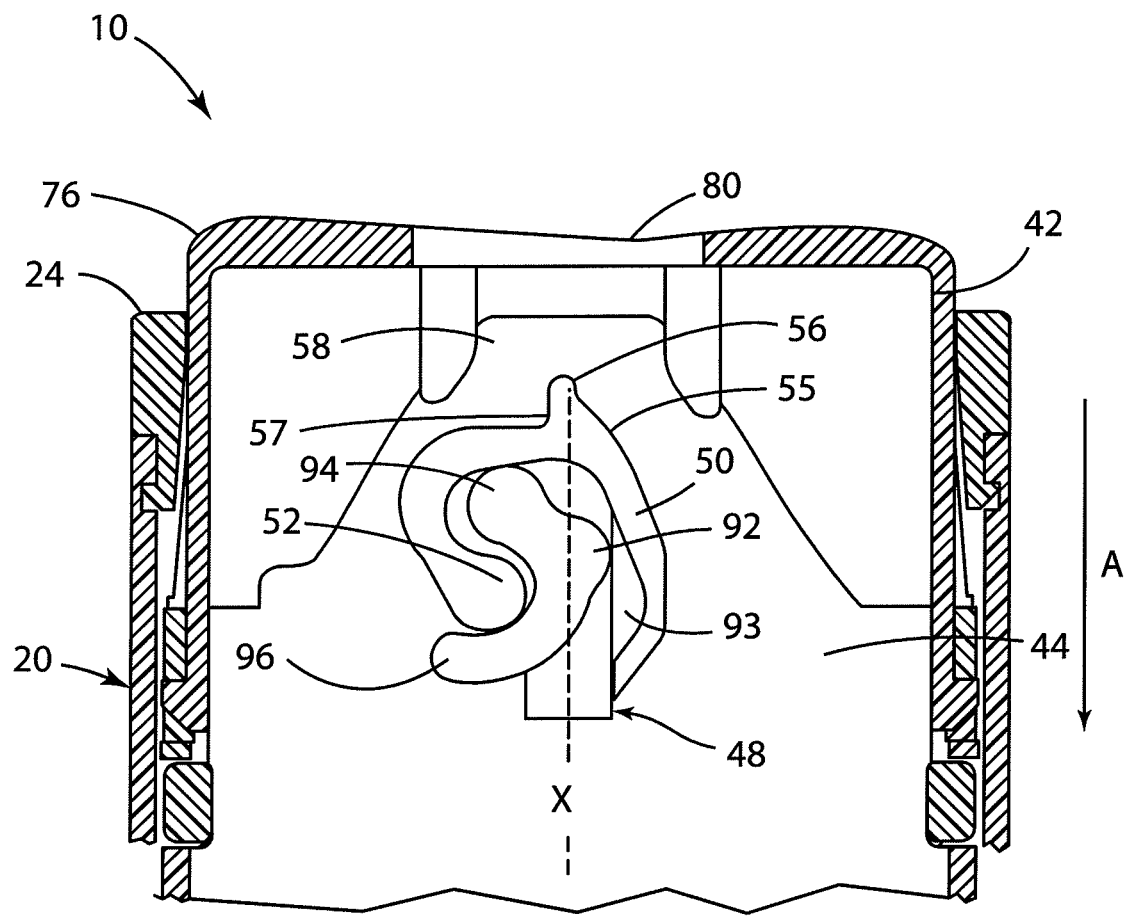
FIG. 8 is simplified schematic view showing the relative position of a cam surface of the roller and a cam ledge of a slider when the roller is at the apex position.

During sliding of the slider from the first position to the second position, the pairs of shafts 92 and 94 appear move upward with respect to their corresponding slot 48 (that is, towards the proximal end 24 of the housing 20). As shown in FIG. 8, as the slider 40 slides in the direction of arrow A to the second position, the cam ledge 50 engages the cam surface 96 on the roller 90. This forces the roller 90 to rotate with respect to the housing about the pair of shafts 92. The gap 93 of the slider 40 allows for relative rotation of the roller 90 with respect to the slider 40 without binding.

Figure 9:
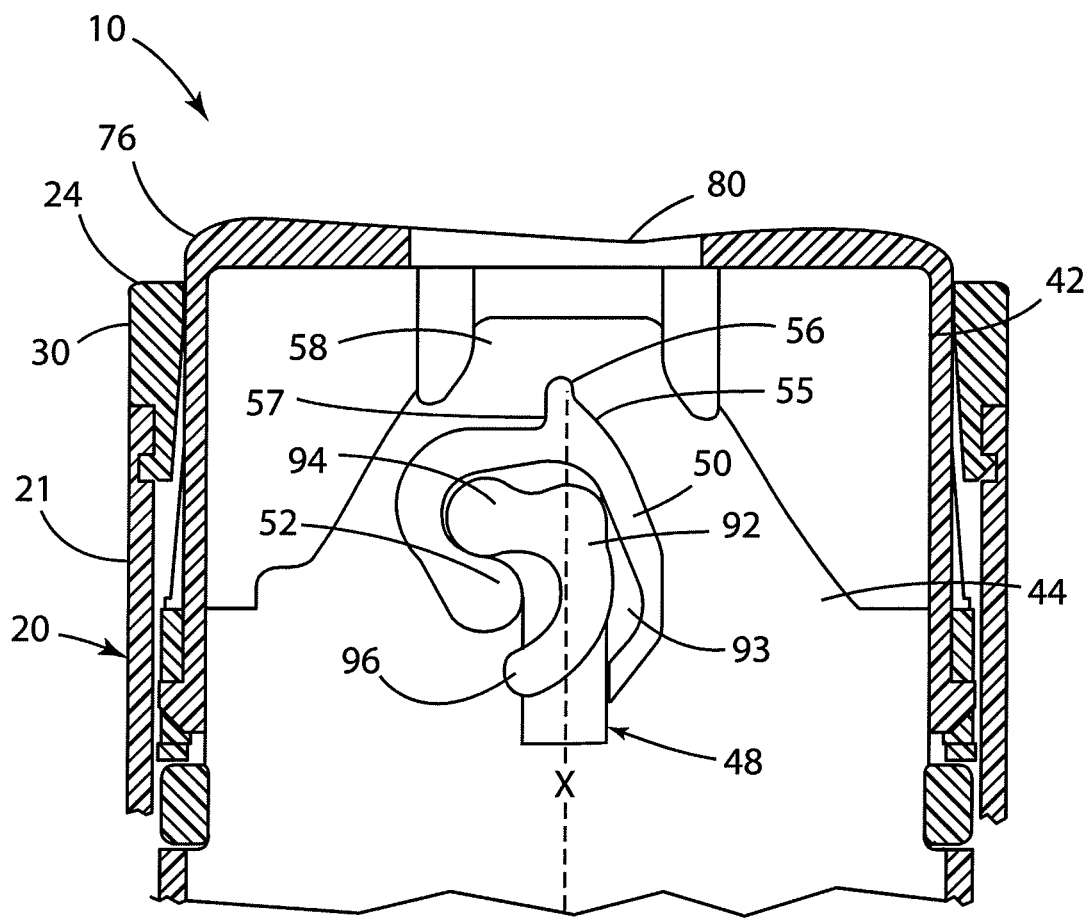
FIG. 9 is simplified schematic view showing the relative position of a cam surface of the roller and a cam ledge of a slider when the roller is at the post-apex segment.

FIG. 9 shows the slider in the third position and the roller in the post-apex segment. Further rotation of the roller around the post-apex segment away from the apex position is limited by the pair of shafts 92, 94 engaging the cam ledge 50 of the slider 40. As noted previously, projections 116 abutting against second wall 57 resist rotation of the roller back to the apex position. In this manner, the blade cannot return to the extended position. Thus, the device acts as a single use device.

From the foregoing disclosure and detailed description of certain embodiments, it will be apparent that various modifications, additions and other alternative embodiments are possible without departing from the true scope and spirit of the invention. The embodiments discussed were chosen and described to provide the best illustration of the principles of the invention and its practical application to thereby enable one of ordinary skill in the art to use the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A contact activated incision device, comprising, in combination:
   a housing defining a cavity, wherein a longitudinal axis extends between a proximal end and a distal end of the housing;
   a slider slidable with respect to the housing along the longitudinal axis and at least partially positioned outside of the housing;
   a roller mounted on the housing and rotatable about a fixed axis perpendicular to the longitudinal axis; and
   a blade assembly mounted on and rotatable with the roller and having a blade, wherein the blade is movable between a retracted position, an extended position and a final position upon moving the slider; and
   wherein, at the retracted position the blade is positioned in the cavity, at the extended position the blade when it exits the slider extends at least partially beyond the proximal end of the housing, and at the final position the blade is positioned in the cavity.

2. The device of claim 1, wherein the movement of the blade from the retracted to the final position does not retrace its steps.

3. A contact activated incision device, comprising, in combination:
   a housing defining a cavity, wherein a longitudinal axis extends between a proximal end and a distal end;
   a slider slidable with respect to the housing along the longitudinal axis and at least partially positioned outside of the housing;
   a first biasing means positioned between the housing and the slider, the first biasing means abutting the slider and biasing the slider towards the proximal end;
   a roller mounted on the housing and rotatable with respect to the housing; and
   a blade assembly mounted on the roller and having a blade, wherein the blade is movable between a retracted position, an extended position where it exits the slider and a final position upon moving the slider;
   wherein at the retracted position the blade is positioned in the cavity, at the extended position the blade extends at least partially beyond the proximal end of the housing, and at the final position the blade is positioned in the cavity and wherein the movement of the blade from the retracted to the final position does not retrace its steps.

4. The device of claim 3, wherein the blade assembly further comprises a second biasing means adapted to bias the blade towards the retracted position.

5. The device of claim 4, wherein the second biasing means is positioned between the blade assembly and the roller.

6. The device of claim 3, wherein the roller is rotatable about a fixed axis perpendicular to the longitudinal axis.

7. The device of any one of claim 1, 3 or 2, wherein the slider is slidable from a first position to a second position and to a third position, and the roller is movable from a start position to an apex position and to a post-apex segment; and
   wherein when the slider is in the first position, the roller is at the start position and the blade is at the retracted position.

8. The device of claim 7, wherein when the roller is at the apex position, the slider is in the second position, and the blade is at the extended position.

9. The device of claim 7, wherein when the roller is at the post-apex segment, the blade is at the final position.

10. The device of claim 7, wherein movement of the slider to the third position urges the roller to rotate past the apex position to the post-apex segment.

11. The device of claim 7, wherein the roller engages the slider such that the roller cannot rotate from the start position until the slider has moved from the first position.

12. The device of claim 7, wherein, the roller has a pair of shafts;

the slider defines a slot adapted to receive the pair of shafts; and the slider receives the pair of shafts within the slot and resists rotation of the roller when the roller is at the start position.

13. The device of claim 12, wherein further rotation of the roller around the post-apex segment away from the apex position is limited by the pair of shafts engaging the cam ledge of the slider.

14. The device of claim 7, wherein the slider further comprises a cam ledge, and the blade assembly has a projection which engages the cam ledge, the cam ledge being positioned between the roller and the projection and the engagement of the projection and the cam ledge being such that as the slider slides from the first position to the second position, the roller rotates, and the blade translates away from the roller.

15. The device of claim 14, wherein the projection engages a second wall of the cam ledge to resist rotation of the roller back from the post-apex segment to the apex position.

16. The device of claim 14, wherein the roller further comprises a cam surface and the cam ledge engages the cam surface to urge rotation of the roller as the slider moves towards the second position.

17. The device of claim 16, wherein the roller further comprises a shaft and the cam ledge engages the shaft after engaging the cam to urge rotation of the roller as the slider moves beyond the second position.

18. The device of claim 1 or claim 2, further comprising a first biasing means positioned between the housing and the slider, the first biasing means abutting the slider and biasing the slider towards the proximal end.

19. The device of any one of claim 1, 3, 4, 5, or 2, wherein the blade is slidable with respect to and independent of the roller.

* * * * *